United States Patent [19]
Shepherd

[11] 4,310,545
[45] Jan. 12, 1982

[54] HYPOLIPIDEMIC AND ANTIATHEROSCLEROTIC 4-(POLYFLUOROALKYLAMINO) PHENYL COMPOUNDS

[75] Inventor: Robert G. Shepherd, South Nyack, N.Y.

[73] Assignee: American Cyanamid Company, Stamford, Conn.

[21] Appl. No.: 93,766

[22] Filed: Nov. 13, 1979

Related U.S. Application Data

[62] Division of Ser. No. 884,941, Mar. 9, 1978, Pat. No. 4,205,085.

[51] Int. Cl.³ .................. C07C 101/60; A61K 31/195; A61K 31/24; C07C 101/62
[52] U.S. Cl. ...................................... 424/310; 562/456; 562/442; 260/348.44; 260/345.8 R; 260/507 R; 546/300; 564/163; 564/157; 564/149; 564/90; 564/105; 564/168; 424/307; 424/319; 424/320; 424/283; 424/278; 424/270; 424/264; 560/47

[58] Field of Search ...................... 562/456, 458, 442; 500/47; 260/348.44, 345.8 R, 507 R; 546/300; 564/163, 157, , 149, 90, 105; 544/64; 424/309, 319, 303, 315, 267, 324, 321, 405 E, 274, 244, 307, 310, 320, 278, 270, 263

[56] References Cited

U.S. PATENT DOCUMENTS

| 3,868,416 | 2/1975 | Albright et al. | 424/319 |
| 3,933,819 | 1/1976 | Toukan et al. | 548/173 |
| 4,205,085 | 5/1980 | Shepherd | 562/456 |
| 4,218,475 | 8/1980 | Wagner et al. | 562/456 |

OTHER PUBLICATIONS

Kawoguchi et al., Chem. Abst., vol. 83, #9471a, (1975).
Parker et al., J. Med. Chem., vol. 20, #6, pp. 781-791, (1977).

Primary Examiner—Natalie Trousof
Assistant Examiner—James H. Reamer
Attorney, Agent, or Firm—Robert P. Raymond

[57] ABSTRACT

This disclosure describes novel 4-(polyfluoroalkylamino)phenyl compounds useful as hypolipidemic and antiatherosclerotic agents.

27 Claims, No Drawings

HYPOLIPIDEMIC AND ANTIATHEROSCLEROTIC 4-(POLYFLUOROALKYLAMINO) PHENYL COMPOUNDS

This is a division, of application Ser. No. 884,941, filed Mar. 9, 1978, now U.S. Pat. No. 4,205,085.

BRIEF SUMMARY OF THE INVENTION

This invention relates to new organic compounds and, more particularly, is concerned with 4-(polyfluoroalkylamino)substituted phenyl compounds which may be represented by the following structural formula

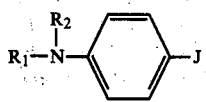

I wherein $R_1$ is a saturated or unsaturated hydrocarbon radical of 7-19 carbon atoms which may be branched or unbranched and which may contain a saturated or unsaturated cycloalkyl group, aid radical containing one or more perfluorinated (—$CF_2$— or —$CF_3$) carbon atoms excluding the carbon adjacent to the nitrogen atom; $R_2$ is selected from the group consisting of hydrogen or a group convertible in vivo thereinto such as methyl, carboxymethyl, acetyl, succinyl, 1-(sodiumsulfo)loweralkyl, 1-(sodiumsulfo)polyhydroxyalkyl, and 3-aryl-1,3-bis-(sodiumsulfo)alkyl; and (a) J is

Z being selected from the group consisting of hydrogen, loweralkyl, hydroxy, loweralkoxy, loweralkoxyloweralkylaminoloweralkoxy, diloweralkylaminoloweralkoxy, (mono- or polyhydroxy)loweralkoxy, allyloxy, 2,3-epoxypropoxy, substituted or unsubstituted benzyloxy, substituted or unsubstituted phenoxy and 3-pyridyloxy, pyridylmethoxy, (mono- or polycarboxy)loweralkoxy, (mono- or polycarboxy)hydroxyloweralkoxy, tetrahydropyranyloxy, (mono- or polyhydroxy)alkylamino, allylamino, propargylamino, 2-sulfoethylamino, (mono- or polycarboxy)loweralkylamino, (mono- or polycarboalkoxy)loweralkylamino, loweralkanoylamino, (substituted or unsubstituted)aroylamino, loweralkanesulfonylamino, (substituted or unsubstituted)arenesulfonylamino, loweralkanoylhydrazino, hydroxylamino, polymethyleneimino, (4-carboethoxy- or 4-carboxy)thiazolidino, loweralkyl bearing one or more carboxy, carboalkoxy, carbamoyl, acyl, sulfinyl, or sulfonyl groups, or (b) Ja is carboxyloweralkyl, carboxyloweralkenyl, carboxyloweralkynyl, carboalkoxyloweralkyl, carboalkoxyloweralkenyl, carboalkoxyloweralkynyl; and the pharmaceutically acceptable non-toxic acid-addition and cationic salts thereof. Lower whenever applied to alkyl, alkanoyl, alkanesulfonyl, alkoxy, alkenyl or alkynyl refers to a chain of 1-6 carbon atoms which may be branched or unbranched. The polyhydroxy and polycarboxy groups referred to above contain 2 to 4 hydroxy or carboxy groups, respectively.

Suitable groups contemplated by the present invention for the polyfluorinated substituent $R_1$ are, for example, 6-(trifluoromethyl)hexyl, 8-(trifluoromethyl)octyl, 10-(trifluoromethyl)decyl, 11-(trifluoromethyl)undecyl, 13-(trifluoromethyl)tridecyl, 15-(trifluoromethyl)pentadecyl, 17-(trifluoromethyl)heptadecyl, 1-(2,2,2-trifluoroethyl)decyl, 1-(2,2,2-trifluoroethyl)pentadecyl, 7-(trifluoromethyl)undecyl, 1-hexyl-11-(trifluoromethyl)undecyl, 3,7-dimethyl-7-(trifluoromethyl)octyl, 11-(pentafluoroethyl)undecyl, 16-(pentafluoroethyl)hexadecyl, 11-(heptafluoropropyl)undecyl, 11-(heptafluoroisopropyl)undecyl, 11-(nonafluorobutyl)undecyl, 11-(undecafluoropentyl)undecyl, 12-fluoro-12-(heptafluoropropyl)-12-(trifluoromethyl)dodecyl, 5-(pentadecafluoroheptyl)pentyl, 7-(pentadecafluoroheptyl)heptyl, 3,3-difluorotetradecyl, 6,6-difluorohexadecyl, 11,11-difluorododecyl, 14,14-difluoropentadecyl, 15,15-difluorohexadecyl, 16,16-difluoroheptadecyl, 11,11-difluoro-16-(trifluoromethyl)hexadecyl, (pentadecafluoroheptyl)methyl, (hentricontafluoropentadecyl)methyl, 11-(trifluoromethyl)-9-undecenyl, 15-(trifluoromethyl)-9-pentadecenyl, 5-(pentadecafluoroheptyl)-4-pentenyl, 6-(pentadecafluoroheptyl)-5-hexenyl, 15-(trifluoromethyl)-7-pentadecenyl, 15-(trifluoromethyl)-12-pentadecenyl, 15-(trifluoromethyl)-4-pentadecynyl, 1-hexyl-9-(trifluoromethyl)-4-nonynyl, 3-(2,2,2-trifluoroethyl)-2,4,4-trimethylcyclopentyl, 3-(trifluoromethyl)-2,4,4-trimethylcyclohexyl, and the like.

Suitable esters contemplated by the present invention are those in which the group Z is methoxy; isopropoxy; 2-ethoxyethoxy; 2-dimethylaminoethoxy; 1-methyl-4-piperidyloxy; 4-pyridylmethoxy; 2,3-dihydroxypropoxy; 2-hydroxypropoxy; 3-hydroxypropoxy; 4-chlorobenzyloxy; 3-methylbenzyloxy; 4-sulfophenoxy; 4-fluorophenoxy; 2,6-dichlorophenoxy; 3-carboxyphenoxy; 2,6-dimethyl-3-pyridyloxy; 6-methoxy-3-pyridyloxy; 2-hydroxy-3-pyridyloxy; 5-carboxy-3-pyridyloxy; 4-cyano-3-pyridyloxy; carboxymethoxy; 1-methoxycarbonylpropoxy; 2-methoxycarbonyl-2-propyl and the like.

Suitable amides contemplated are those in which the group Z is 2,3-dihydroxypropylamino; carboxymethylamino, acetylamino, benzoylamino, 4-chlorobenzoylamino; methanesulfonylamino; phenylsulfonylamino, 1-piperidyl, and the like.

Suitable keto-acids and keto-esters contemplated by the present invention are those in which the radical Z is selected from the group consisting of carboxymethyl carboxyethyl; 2-carboethoxy-2-propyl; dicarboethoxymethyl; carboethoxyvinyl and the like. Suitable alkanoic, alkenoic and alkynoic acids and esters are those in which the radical J is selected from the group consisting of 4-carboxybutyl; 2-carboethoxyethyl; 2-carboxyvinyl, 2-carboethoxyethynyl, and the like.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel 4-(polyfluoroalkylamino)phenyl compounds of the present invention. These compounds may be utilized either as such or in the form of a pharmaceutically acceptable salt with an organic or inorganic acid or base. The invention also contemplates a method for lowering serum lipids and for ameliorating atherosclerosis in mammals by the administration of said compounds.

BACKGROUND OF THE INVENTION

Considerable effort has been directed to recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, must importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involed in coronary heart disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al., 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine, and nicotinic acid [Levy and Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. 4-(Alkylamino)benzoic acids and esters are the subject of our U.S. Pat. No. 3,868,416 issued Feb. 25, 1975.

DETAILED DESCRIPTION OF THE INVENTION

The compounds of this invention are new and novel 4-(polyfluoroalkylamino)phenyl compounds and have useful biological and pharmacological properties. No hypolipidemic activity has been reported in the literature for these compounds and they are different in structure from other hypolipidemic agents. The compounds of this invention lower serum-lipid concentrations and also minimize atheroma formation in the aorta. These compounds provide the oral administration required of hypolipidemic agents, which patients usually take for many years. The novel compounds of this invention are adequately and reliably absorbed from the gastrointestinal tract with little, if any, gastrointestinal irritation.

We have now found that certain members of this class of compound can safely and effectively lower both serum sterols and triglycerides in warm-blooded animals. Such actions on serum-lipid components are considered to be very useful in the treatment of atherosclerosis, especially in contrast to available drugs whose action is much more limited. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The 4-(polyfluoroalkylamino)phenyl compounds of the present invention are, in general, white crystalline solids having characteristic melting points and absorption spectra. They are soluble in organic solvents such as lower alkanols, chloroform, toluene, dimethylformamide, and the like but are generally not very soluble in water.

The novel compounds of the present invention which are organic bases may be converted to their non-toxic acid-addition salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, tartaric, ascorbic, and the like.

The novel compounds of the present invention in their acidic forms or those which contain acidic substituents are converted to their organic or inorganic cationic salts for therapeutic use. The sodium or potassium salts which are formed in solution in the course of hydrolysis of their esters can be isolated as the solid alkali metal salts by cooling. Where it is desirable to purify a compound in the form of the acid, the salt is conveniently formed by treating its solution w-th exactly one equivalent of base and evaporation of lyophilization. Alkaline earth salts are prepared similarly, often using their acetate salts as a conveniently soluble form. Organic base salts such as those of N-methylglucamine are prepared by dissolving equimolar amounts of the acid and the base in hot ethanol or aqueous alcohols and cooling to crystallization.

Many of the polyfluorinated-alkyl halides required as intermediates for the syntheses of the novel 4-(polyfluoroalkylamino)phenyl compounds of the present invention are prepared from the corresponding hydroxy acids, for example, reaction of 16-hydroxyhexadecanoic acid with hydrogen bromide followed by sulfur tetrafluoride affords 15-(trifluoromethyl)pentadecyl bromide. Certain of the polyfluorinated-alkyl halides or methanesulfonates are prepared from the corresponding alcohols which in turn are obtained from the appropriate polyfluorinated carboxylic acids, for example, reduction of 11-(pentafluoroethyl)undecanoic acid with diborane or a metal hydride affords 11-(pentafluoroethyl)undecanol which may then be converted to 11-(pentafluoroethyl)undecyl bromide by reaction with hydrogen bromide or alternatively to 1-(methanesulfonyloxy)-11-(pentafluoroethyl)undecane by reaction with methanesulfonyl chloride. Other polyfluorinated-alkyl halides are prepared by the reaction of sulfur tetrafluoride with ketones, for example, reaction of 17-bromo-11-oxoheptadecanoic acid (obtained by the peroxide-catalyzed addition of hydrogen bromide to 11-oxo-16-heptadecenoic acid) with sulfur tetrafluoride affords 16-trifluoromethyl)-11,11-difluorohexadecyl bromide. Similarly, 15-bromo-2-pentadecanone (obtained by alkylation of 14-bromotetradecanoyl chloride with dimethyl cadmium) yields 14,14-difluoropentadecyl bromide.

Many of the novel 4-(polyfluoroalkylamino)phenyl compounds of the present invention may be prepared by reaction of the appropriate 4-aminophenyl compound with a suitable alkylating agent such as an alkyl halide, sulfate, tosylate, or trifluoromethanesulfonate with or without a solvent at 30° C. to 150° C. Appropriate 4-aminophenyl compounds are, for example, ethyl 4-aminobenzoate; 2,3-dihydroxypropyl 4-aminobenzoate; phenyl 4-aminobenzoate; 1-(4-aminobenzoyl)pyrrolidine; and ethyl 4-(4-aminophenyl)butyrate. Suitable solvents are loweralkanols, N,N-dimethylformamide, N,N-dimethylacetamide, 1,2-dimethoxyethane, acetonitrile, toluene, benzene, hexamethylphosphoramide and the like. The reaction may be carried out with two equivalents of the 4-aminophenyl compound or with one equivalent of the compound plus one equivalent of a base such as an alkali carbonate or bicarbonate or an unreactive organic base such as diisopropylethylamine or alternatively with a catalytic amount of copper powder when an alkyl halide is used as the alkylating agent. Similarly, alkylation of the sodium salt (formed with sodium hydride) of either the amino group of a 4-aminophenyl compound or the anilide moiety of a 4-(acetylamino)phenyl compound yields the novel 4-(polyfluoroalkylamino)phenyl compounds or an N-acetyl derivative thereof. Removal of the N-acetyl group by conventional hydrolytic methods affords the desired 4-(polyfluoroalkylamino)phenyl compounds.

Alternative methods of preparation of these compounds are by reductive alkylation of a 4-aminophenyl compound, which may be generated in situ by reduction of a 4-aminophenyl precursor such as a 4-nitrophenyl compound and the like or by a metal hydride reduction of a 4-(acylamino)phenyl compound. For example, 15-(trifluoromethyl)pentadecanal or another carbonylalkane and 4-aminobenzoic acid are reduced under 1–10 atmospheres of hydrogen using an activated metal catalywt or a metal hydride such as sodium borohydride forming 4-[15-(trifluoromethyl)pentadecylamino]benzoic acid and the like. Diborane reduction of 4-(polyfluoroalkanoylamino)phenyl compounds such as ethyl 4-[15-(trifluoromethyl)pentadecanoylamino]benzoate at room temperature or above for 1–6 hours yields the corresponding 4-(polyfluoroalkylamino)phenyl compounds such as ethyl 4-[15-(trifluoromethyl)pentadecylamino]benzoate. The 4-(polyfluoroalkanoylamino)phenyl compounds used in these reductions are prepared by acylation of the appropriate 4-aminophenyl compounds with suitable acylating agents, such as polyfluoroalkanoyl halides. To prepare the 4-(polyfluoroalkylamino)phenyl alkenoic and alkynoic acids it is advantageous to form the corresponding polyfluoroalkylchloroimide from the 4-(polyfluoroalkanoylamino)phenyl compounds using phosphorus oxychloride and base, and then reduce the polyfluoroalkylchloroimide moiety to a polyfluoroalkylamino group with sodium borohydride.

A method useful for the introduction of the polyfluoroalkylamino group into aromatic compounds is nucleophilic aromatic substitution. An example of this method is the reaction of 15-(trifluoromethyl)pentadecylamine (or the anion derived therefrom by treatment with a strong base) with ethyl 4-fluorobenzoate to yield ethyl 4-[15-(trifluoromethyl)pentadecylamino]benzoate. In certain instances an amine such as 15-(trifluoromethyl)pentadecylamine may be reacted with a benzyne such as that derived from ethyl 4-bromobenzoate by treatment with sodium amide to yield the 4-(polyfluoroalkylamino)phenyl compound, in this case ethyl 4-[15-(trifluoromethyl)pentadecylamino]benzoate.

The 4-(polyfluoroalkylamino)benzoic, benzoylalkanoic, and phenylalkanoic acids of this invention are often prepared from the corresponding p-aminobenzoic, benzoylalkanoic, and phenylalkanoic acids by the sequence involving esterification of the amino acid with ethanol in the presence of boron trifluoride etherate, followed by alkylation of the amino function by the methods above. The free acids are then liberated by hydrolysis of the ester with aqueous alcoholic sodium hydroxide at 80° for 2–10 hours followed by acidification. The acids obtained by this procedure may be converted to the corresponding metallic cationic salts. For example, the sodium salt may be prepared by reaction of the acid with sodium hydroxide in a mixture of ethanol and water.

Alternatively, the acids of this invention may be prepared by hydrolysis of the corresponding nitriles or various amides, imidates or oxazolines. The carboxylic acid moiety may also be generated by oxidation of the corresponding aldehydes, acetophenones, benzyl alcohols, or toluenes, most often with the use of an amine-protecting group such as trifluoroacetyl or t-butyloxycarbonyl.

The carboxaldehydes of this invention may be prepared by several methods among which is alkylation of the corresponding acetal by the methods above followed by hydrolysis of the resulting 4-(polyfluoroalkylamino)phenyl acetal to the desired aldehyde. Aldehydes may also be prepared by reduction of the appropriate nitriles. For example, treatment of 4-[15-(trifluoromethyl)pentadecylamino]benzonitrile with stannic chloride and anhydrous hydrogen chloride gas, followed by hydrolysis in hot water provides 4-[15-(trifluoromethyl)pentadecylamino]benzaldehyde. These reductions are also conveniently carried out with hydrides such as diisobutyl aluminum hydride.

The novel esters and amides of the present invention may readily be prepared by treating a derivative of the corresponding carboxylic acid, such as the acid halide, mixed acid anhydride or activated ester or amide with the appropriate alcohol or amine, respectively. These reactions may be carried out in an inert solvent at a temperature of 50°-125° C. for 30 minutes to 18 hours or more. In the case of the acid halide and other acid-forming acylating agents, the reaction is carried out in the presence of an acid scavenger such as diisopropylethylamine; 4-dimethylaminopyridine; pyridine; triethylamine; finely powdered sodium carbonate and the like. A protecting group on the amino nitrogen is used for best results. The simplest protecting group is provided by protonation of the amine to yield an anilinium salt prior to or during formation of the acylating form of the carboxyl group. Acylation of the amino group by carefully selected acyl groups such as carbobenzyloxy, carbo-t-butoxy, and trifluoroacetyl provides protection of this group from self-acylation during amide or ester formation. These protecting groups are then removed by catalytic hydrogenation, mild acid treatment, and mild alkali treatment, respectively. Other N-acyl protecting groups such as acetyl and succinoyl may be used and these are removed by conventional methods. Activated esters and amides, useful to synthesize the esters and amides of the present invention, are those containing carboxymethyl, 4-nitrophenyl, N-oxysuccinimide and 1-imidazolyl groups and the like. In certain cases, treatment of the acids with an excess of an appropriate hydroxy-containing substrate in the presence of a Lewis or mineral acid such as boron trifluoride, sulfuric acid or hydrochloric acid affords the corresponding esters. Ordinary esters such as the methyl and ethyl esters are sufficiently reactive to form the amides of the 4-(polyfluoroalkylamino)benzoic acids and highly reactive amine substrates such as hydroxylamine, hydrazines and certain alkyl primary amines. With certain kinds of substrates in order to form amides it is necessary to first form the alkali metal or strong organic base salts of these substrates prior to reacting them with the various aforementioned acylating forms of the 4-(polyfluoroalkylamino)benzoic acids. For example, the aminoalkanecarboxylic and aminoalkanesulfonic acids are zwitterionic and must be converted to their salts, suitably in situ. They may also be used in the form of their esters and then hydrolyzed after amide formation. Certain substrates which are neutral, like the carboxamides, or slightly acidic, like the alkane or arene sulfonamides, are converted to reactive sodium salts by reaction with sodium hydride or other basic reagents.

The α-substituted 4-(polyfluoroalkylamino)acetophenones of the invention are prepared by reaction of a derivative of the appropriate benzoic acid, such as 4-[15-(trifluoromethyl)pentadecylamino]benzoyl chloride hydrochloride, with two or more equivalents of the reactive salt of an acidic methylene compound, for example the sodium salt of diethyl malonate. Other benzoic acid derivatives are also suitable for this reaction, such as 4-[N-trifluoroacetyl(polyfluoroalkyl)amino]benzoyl chloride, a 4-[N-tert-butyloxycarbonyl(polyfluoroalkyl)amino]benzoyl chloride or a methyl 4-(polyfluoroalkylamino)benzoate ester. In some cases the final step in the preparation of the α-substituted 4-(polyfluoroalkylamino)acetophenones is the removal of the nitrogen-protecting group. In other cases, hydrolysis of one or more of the ester groups in the acylation product affords an unstable polycarboxylic acid which undergoes decarboxylation to allow the preparation of another acetophenone derivative. For example, the reaction of tert-butyl ethyl 4-[15-(trifluoromethyl)pentadecylamino]benzoylmalonate with trifluoroacetic acid affords ethyl 4-[15-trifluoromethyl)-pentadecylamino]benzoylacetate. In other cases, hydrolysis of one or more of the ester groups allows the preparation of the corresponding acid derivative. For example, the hydrolysis of ethyl 4-[15-(trifluoromethyl)pentadecylamino]benzoylacetate yields 4-[15-(trifluoromethyl)pentadecylamino]benzoylacetic acid.

An alternative procedure for preparing certain α-substituted-4-(polyfluoroalkylamino)acetophenones is alkylation of the corresponding 4-aminoacetophenone by the methods above. For example, alkylation of methyl 3-(4-aminobenzoyl)propionate with 15-(trifluoromethyl)bromide yields methyl 3-{4-[15-(trifluoromethyl)-pentadecylamino]benzoyl}propionate. The related carboxylic acids are then obtained by hydrolysis. Certain of these acids are particularly useful for the preparation of [4-(polyfluoroalkylamino)phenyl]alkanoic acids by reduction. For example, the Clemmensen of Wolff-Kishner reduction of 3-{4-[15-(trifluoromethyl)pentadecylamino]benzoyl}propionic acid yields 4-{4-[15-(trifluoromethyl)pentadecylamino]phenyl}butyric acid.

The [4-(polyfluoroalkylamino)phenyl]alkenoic acids may be prepared by condensation of the appropriate aldehydes or by dehydration of the corresponding substituted-phenyl-hydroxyalkanoic acids. For examle, ethyl 5-{4-[15-(trifluoromethyl)pentadecylamino]-phenyl}-2,4-pentadienoate is obtained by the Wittig reaction of 4-[15-(trifluoromethyl)pentadecylamino]-benzaldehyde with the Wittig reagent, triethyl 4-phosphonocrotonate. Alternatively, these alkenoic acids are obtained by heating 4-[N-polyfluoroalkyl-N-(methyl or acetyl)amino]benzaldehydes with the sodium salt of the carbanion of ethyl acetate or with a mixture of ethyl acetate, acetic anhydride and potassium acetate. The second method is illustrated by dehydration of ethyl 3-{4-[15-(trifluoromethyl)pentadecylamino]phenyl}-3-hydroxypropionate to yield ethyl 4-[15-(trifluoromethyl)pentadecylamino]cinnamate.

The acetylenic analogs are prepared by dehydrobromination of the side-chain vic-dibrominated alkanoic acid. For example, dehydrobromination of ethyl 3-{4-[15-(trifluoromethyl)pentadecylamino]phenyl}-2,3-dibromopropionate, its isomers or N-acyl analogs yields ethyl 3-{4-[15-(trifluoromethyl)pentadecylamino]-phenyl}pripiolate. The acetylenic acids are also formed from (4-polyfluoroalkylamino)phenylacetylene metal salts by carboxylation with carbon dioxide. The 4-(polyfluoroalkylamino)phenylacetylenes are also used by N-acylating with t-butyl azidoformate followed by conversion to the lithium acetylide salt and subsequent reaction of the lithium salt with boron trifluoride etherate in tetrahydrofuran at −20° C. to form tris-[4-(polyfluoroalkylamino)phenylethynyl]boranes. The tetrahydrofuran solution of the borane is in turn reacted with ethyl diazoacetate, followed by water to yield ethyl 4-[4-(polyfluoroalkylamino)phenyl]butynoate.

The 4-(polyfluoroalkylamino)phenylalkanoic acids, amides, or esters are also prepared by catalytic reduction at 1 to 10 atmospheres of hydrogen of the corresponding alkenoic or alkynoic derivatives.

The 4-(polyfluoroalkylamino)phenylalkenoic acids and derivatives are prepared by Friedel-Crafts acylation of the N-acyl-N-alkylanilines with the appropriate dicarboxylic acid anhydride or half acid chloride. The 4-(polyfluoroalkylamino)benzoylalkanoic acids or esters, obtained by this and by other syntheses, may be converted to the 4(polyfluoroalkylamino)phenylalkanoic acids by reduction with (a) hydrazine and alkali in diethylene glycol at 140° for 3 hours, (b) zinc amalgam and ethanolic hydrochloric acid at 60° for 5 hours, (c) red phosphorus and hydriodic acid, or (d) ketalization with 1,2-ethanedithiol followed by Raney nickel desulfurization. The amides of the 4-(polyfluoroalkylamino)-phenylalkanoic acids are prepared by heating the corresponding 4-(polyfluoroalkylamino)phenyl alkyl ketones with aqueous alcoholic ammonium polysulfide followed by hydrolysis to yield the acids with the same number of carbon atoms as the ketone. These acids are also prepared by reacting 4-(N-t-butyloxycarbonyl-N-polyfluoroalkylamino)phenylmagnesium halides with 2-(3-halopropyl)-2-oxazolines, followed by mild acid removal of 2-oxazolinyl and t-butoxycarbonyl protecting groups. Similarly, the above Grignard reagent can be reacted with 3-bromotriethylorthopropionate in the presence of dilithiumtetrachlorocuprate to yield the desired acids after removal of the protecting groups from the amino and carboxyl groups.

The novel compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kologram of body weight per day, and such dosage units are employed that a total of from about 0.35 gram to about 7.0 grams of the active compound, for a subject of about 70 kg. of body weight, are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypocholesteremic and antiatherosclerotic effect than the aforementioned adjuvants and synthetic medicaments. It is not known how these novel compounds operate in the blood serum and no theory of why these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propyl parabens as preservatives, a dye, and flavoring such as cherry or orange flavor. Of course, any material used in preparing any dosage-unit form should be pharmaceutically pure and substantially non-toxic in the amounts employed. In addition, the active ingredients may be incorporated into sustained-release preparations and formulations.

The invention will be described in greater detail in conjunction with thx following specific Examples.

EXAMPLE 1

16-Bromohexadecanoic acid

A mixture of 18 g. of 16-hydroxyhexadecanoic acid and 160 g. of 30–34% hydrogen bromide in acetic acid is treated with 32 ml. of concentrated sulfuric acid and stirred at ambient temperature for 18 hours. The solution is stirred under reflux for 7 hours and then poured into 500 ml. of ice-water and filtered. A methylene chloride solution of the product is Darco clarified, dried over magnesium sulfate, and evaporated. Crystallization of the residue from ether-petroleum ether and then acetonitrile affords 16-bromohexadecanoic acid as a white solid.

EXAMPLE 2

15-(Trifluoromethyl)pentadecyl bromide

A 25.0 g. quantity of 16-bromohexadecanoic acid is placed in a 2 liter stainless steel bomb and after flushing with nitrogen and cooling the bomb in dry-ice, 66 g. of sulfur tetrafluoride is introduced and the sealed bomb is heated with shaking at 118° C. for 6 hours. The bomb is allowed to cool and opened and volatile material is allowed to evaporate. The residue is partitioned between water and ether and the ether layer is separated, dried over anhydrous magnesium sulfate and evaporated. The residue is distilled to yield 15-(trifluoromethyl)pentadecyl bromide as a clear, colorless liquid.

EXAMPLE 3

(Pentadecafluoroheptyl)(trifluoromethanesulfonyloxy)methane

A mixture of 40 g of (pentadecafluoroheptyl)methanol, 11 g. of triethylamine, and 200 ml. of methylene chloride is stirred at −20° C. while a solution of 18 g. of trifluoromethanesulfonyl chloride in 50 ml. of methylene chloride is added. The solution is stirred for one hour at room temperature and then washed with ice-cold 10% hydrochloric acid, saturated aqueous sodium bicarbonate solution, and water; dried over anhydrous magnesium sulfate; and evaporated. The residual brown liquid is distilled to yield the product as a colorless liquid.

EXAMPLE 4

11-(Pentafluoroethyl)undecanol

A solution of 5 g. of 11-(pentafluoroethyl)undecanoic acid in 20 ml. of tetrahydrofuran is stirred at 0° C. while 16 ml. of 1 M borane in tetrahydrofuran is added during 15 minutes. The mixture is stirred for 18 hours at ambient temperature, poured into ice-water, and extracted with ether. The dried extract is evaporated and the residual oil crystallized from hexane to yield 11-(pentadecafluoroethyl)undecanol as a white solid.

EXAMPLE 5

11-(Pentafluoroethyl)-1-(methanesulfonyloxy)undecane

To a solution of 15 g. of 11-(pentafluoroethyl)undecanol and triethylamine (14 ml.) in dry methylene chloride (320 ml.) at −8° C. is added methanesulfonylchloride (5.73 ml.), dropwise. The reaction mixture is stirred at −10° C. for 30 minutes and then diluted with methylene chloride, extracted with ice-water (250 ml.), followed by cold 10% hydrochloric acid (200 ml.); cold saturated sodium bicarbonate (200 ml.) and cold saturated sodium chloride solution (200 ml.). The organic layer is separated, dried over anhydrous magnesium sulfate, and evaporated to yield the methanesulfonate as a light yellow oil.

EXAMPLE 6

6-Oxohexadecyl bromide

The Grignard reagent prepared from 60 g. of decyl bromide, 5.6 g. of magnesium, and 200 ml. of ether is treated with 27 g. of cadmium chloride and the solution is stirred under reflux for 30 minutes. The solvent is replaced by distillation with toluene, and the toluene solution is treated with 29 g. of 6-bromohexanoyl chloride and stirred under reflux for 30 minutes. The mixture is cooled, diluted with 200 ml. of 10% sulfuric acid, and extracted with ether. The extracts are dried and evaporated and the residual oil distilled in vacuo to yield 6-oxohexadecyl bromide as a light yellow oil.

EXAMPLE 7

6,6-Difluorohexadecyl bromide

In the manner of Example 2, 6-oxohexadecyl bromide is converted to 6,6-difluorohexadecyl bromide.

EXAMPLE 8

Ethyl 4-[15-(trifluoromethyl)pentadecylamino]benzoate

A mixture of 18.5 g. of 15-(trifluoromethyl)pentadecyl bromide, 17.0 g. of ethyl 4-aminobenzoate, 7.1 g. of potassium carbonate, and 75 ml. of hexamethylphosphoramide is stirred for 16 hours at 120° C., allowed to cool, diluted with water, and filtered. The solid is dissolved in methylene chloride and the solution is dried over anhydrous magnesium sulfate and evaporated. The residual brown oil is crystallized from ethanol and recrystallized from acetonitrile to yield the product as a white solid.

EXAMPLE 9

4-[15-(Trifluoromethyl)pentadecylamino]benzoic acid

A mixture of 6.0 g. of ethyl 4-[15-(trifluoromethyl)pentadecylamino]benzoate, 4.0 g. of potassium hydroxide and 50 ml. of ethanol is stirred at 80° C. for 4 hours. The mixture is diluted with water and adjusted to pH 5.5 by the addition of concentrated hydrochloric acid. Cooling and filtration affords a solid which is recrystallized from acetone to yield the product as a white solid.

EXAMPLE 10

Ethyl 4-[(pentadecafluoroheptyl)methylamino]benzoate

A solution of 45 g. of (pentadecafluoroheptyl)(trifluoromethanesulfonyloxy)methane and 28 g. of ethyl 4-aminobenzoate in 50 ml. of hexamethylphosphoramide is stirred at 120° C. for 72 hours, diluted with water, and filtered. A methylene chloride solution of the solid is dried over anhydrous magnesium sulfate and evaporated. The residue is recrystallized from acetonitrile to yield the product as a white solid.

EXAMPLE 11

4[(Pentadecafluoroheptyl)methylamino]benzoic acid

Hydrolysis of ethyl 4-[(pentadecafluoroheptyl)methylamino]benzoate by the method of Example 9 affords 4-[(pentadecafluoroheptyl)methylamino]benzoic acid as a white solid.

EXAMPLE 12

Ethyl 4-[11-(pentafluoroethyl)undecylamino]benzoate

A solution of 18.1 g. of 11-(pentafluoroethyl)-1-(methanesulfonyloxy)undecane and 19.8 g. of ethyl p-aminobenzoate in hexamethylphosphoramide is heated at 120° C. for 20 hours. After cooling, the reaction mixture is diluted with ethanol:water (1:1) (30 ml.) and chilled. More ethanol is added, the mixture is filtered and the solid residue is recrystallized from ethanol to yield the product as a white solid.

EXAMPLE 13

4-[11-(Pentafluoroethyl)undecylamino]benzoic acid

Hydrolysis of ethyl 4-[11-(pentafluoroethyl)undecylamino]benzoate in the manner of Example 9 affords 4-[11-(pentafluoroethyl)undecylamino]benzoic acid as a white solid.

TABLE I

The following benzoic acids are prepared from the corresponding benzoate esters by the method of Example 9. The requisite benzoate esters are prepared from 4-aminobenzoate esters and the appropriate halide, trifluoromethanesulfonate, or methanesulfonate by the methods of Examples 8, 10, and 12, respectively. Polyfluoroalkyl halides, trifluoromethanesulfonates, and methanesulfonates required for these reactions are prepared by the methods of Examples 1–7.

| Example No. | Compound |
|---|---|
| 14 | 4-[6-(Trifluoromethyl)hexylamino]benzoic acid |

TABLE I-continued

The following benzoic acids are prepared from the corresponding benzoate esters by the method of Example 9. The requisite benzoate esters are prepared from 4-aminobenzoate esters and the appropriate halide, trifluoromethanesulfonate, or methanesulfonate by the methods of Examples 8, 10, and 12, respectively. Polyfluoroalkyl halides, trifluoromethanesulfonates, and methanesulfonates required for these reactions are prepared by the methods of Examples 1–7.

| Example No. | Compound |
|---|---|
| 15 | 4-[7-(Trifluoromethyl)heptylamino]benzoic acid |
| 16 | 4-[8-(Trifluoromethyl)octylamino]benzoic acid |
| 17 | 4-[9-(Trifluoromethyl)nonylamino]benzoic acid |
| 18 | 4-[10-(Trifluoromethyl)decylamino]benzoic acid |
| 19 | 4-[11-(Trifluoromethyl)undecylamino]benzoic acid |
| 20 | 4-[12-(Trifluoromethyl)dodecylamino]benzoic acid |
| 21 | 4-[13-(Trifluoromethyl)tridecylamino]benzoic acid |
| 22 | 4-[14-(Trifluoromethyl)tetradecylamino]benzoic acid |
| 23 | 2-[16-(Trifluoromethyl)hexadecylamino]benzoic acid |
| 24 | 4-[17-(Trifluoromethyl)heptadecylamino]benzoic acid |
| 25 | 4-[18-(Trifluoromethyl)octadecylamino]benzoic acid |
| 26 | 4-[1-(2,2,2-Trifluoroethyl)decylamino]benzoic acid |
| 27 | 4-[1-(2,2,2-Trifluoroethyl)tridecylamino]benzoic acid |
| 28 | 4-[1-(2,2,2-Trifluoroethyl)pentadecylamino]benzoic acid |
| 29 | 4-[7-(Trifluoromethyl)undecylamino]benzoic acid |
| 30 | 4-[1-Hexyl-11-(trifluoromethyl)undecylamino]benzoic acid |
| 31 | 4-[3,7-Dimethyl-7-(trifluoromethyl)octylamino]benzoic acid |
| 32 | 4-[16-(Pentafluoroethyl)hexadecylamino]benzoic acid |
| 33 | 4-[11-(Heptafluoropropyl)undecylamino]benzoic acid |
| 34 | 4-[11-(Heptafluoroisopropyl)undecylamino]benzoic acid |
| 35 | 4-[11-)Nonafluorobutyl)undecylamino]benzoic acid |
| 36 | 4-[11-(Undecafluoropentyl)undecylamino]benzoic acid |
| 37 | 4-[12-Fluoro-12-(heptafluoropropyl)-12-(trifluoromethyl)dodecylamino]benzoic acid |
| 38 | 4-[5-(Pentadecafluoroheptyl)pentylamino]benzoic acid |
| 39 | 4-[7-(Pentadecafluoroheptyl)heptylamino]benzoic acid |
| 40 | 4-(3,3-Difluorotetradecylamino)benzoic acid |
| 41 | 4-(6,6-Difluorohexadecylamino)benzoic acid |
| 42 | 4-(11,11-Difluorododecylamino)benzoic acid |
| 43 | 4-(14,14-Difluoropentadecylamino)benzoic acid |
| 44 | 4-(15,15-Difluorohexadecylamino)benzoic acid |
| 45 | 4-((16,16-Difluoroheptadecylamino)benzoic acid |
| 46 | 4-[11,11-Difluoro-16-(trifluoromethyl)hexadecylamino]benzoic acid |
| 47 | 4-[(Hentricontafluoropentadecyl)methylamino]benzoic acid |
| 48 | 4-[11-(Trifluoromethyl)-9-undecenylamino]benzoic acid |
| 49 | 4-[15-(Trifluoromethyl)-9-pentadecenylamino]benzoic acid |
| 50 | 4-[5-(Pentadecafluoroheptyl)-4-pentenylamino]benzoic acid |
| 51 | 4-[6-(Pentadecafluoroheptyl)-5-hexenylamino]benzoic acid |
| 52 | 4-[15-(Trifluoromethyl)-7-pentadecenylamino]benzoic acid |
| 53 | 4-[15-(Trifluoromethyl)-12-pentadecenylamino]benzoic acid |
| 54 | 4-[15-(Trifluoromethyl)-4-pentadecynylamino]benzoic acid |
| 55 | 4-[1-Hexyl-9-(trifluoromethyl-4-nonynylamino]benzoic acid |
| 56 | 4-[3-(2,2,2-Trifluoroethyl)-2,4,4-trimethyl- |

TABLE I-continued

The following benzoic acids are prepared from the corresponding benzoate esters by the method of Example 9. The requisite benzoate esters are prepared from 4-aminobenzoate esters and the appropriate halide, trifluoromethanesulfonate, or methanesulfonate by the methods of Examples 8, 10, and 12, respectively. Polyfluoroalkyl halides, trifluoromethanesulfonates, and methanesulfonates required for these reactions are prepared by the methods of Examples 1–7.

| Example No. | Compound |
|---|---|
|  | cyclopentylamino]benzoic acid |
| 57 | 4-[3-(Trifluoromethyl)-2,4,4-trimethylcyclohexylamino]benzoic acid |

EXAMPLE 58

4-[15-(Trifluoromethyl)pentadecylamino]benzaldehyde

A solution of 4-aminobenzonitrile (11.8 g.) and 15-(trifluoromethyl)pentadecyl bromide (15.3 g.) in hexamethylphosphoramide (200 ml.) is heated under an atmosphere of nitrogen in an oil bath maintained at 120° C. for 22 hours. The reaction mixture is cooled to room temperature and water is added gradually. The mixture is then chilled in an ice-bath and filtered. The solid is washed thoroughly with water and dried. The solid is recrystallized from ether-hexane to yield 4-[(15-trifluoromethyl)pentadecylamino]benzonitrile as a pale yellow solid.

Di-isobutylaluminum hydride (54 ml., 25% solution in toluene) is added with stirring to a solution of the nitrile under a nitrogen atmosphere. The temperature rises to 40° C. during the addition which takes 30 minutes and the reaction is then stirred for 1 hour. A solution of methanol in toluene (50 ml., 1:1) is added during 30 minutes and the mixture is poured into vigorously stirred ice-cold aqueous sulfuric acid (500 ml., 5%). After 10 minutes, diatomaceous earth (30 g.) is added, the mixture filtered and the organic layer separated. The aqueous solution is extracted twice with toluene (100 ml.) and the combined organic layers are washed with aqueous sodium bicarbonate, dried over magnesium sulfate, decolorized with charcoal, filtered and evaporated in vaco to give a light yellow crystalline solid. Recrystallization from hexane affords 4-[15-(trifluoromethyl)pentadecylamino]benzaldehyde as a white solid.

TABLE II

The following benzaldehydes are prepared from 4-aminobenzonitrile and the appropriate polyfluoroalkyl halide by the method of Example 58.

| Example No. | Compound |
|---|---|
| 59 | 4-[6-(Trifluoromethyl)hexylamino]benzaldehyde |
| 60 | 4-[11-(Trifluoromethyl)undecylamino]benzaldehyde |
| 61 | 4-[17-(Trifluoromethyl)heptadecylamino]benzaldehyde |
| 62 | 4-[7-(Trifluoromethyl)undecylamino]benzaldehyde |
| 63 | 4-[11-(Pentafluoroethyl)undecylamino]benzaldehyde |
| 64 | 4-[16-(Pentafluoroethyl)hexadecylamino]benzaldehyde |
| 65 | 4-[5-(Pentadecafluoroheptyl)pentylamino]benzaldehyde |
| 66 | 4-(6,6-Difluorohexadecylamino)benzaldehyde |
| 67 | 4-(14,14-Difluoropentadecylamino)benzaldehyde |
| 68 | 4-[(Pentadecafluoroheptyl)methylamino]benzaldehyde |
| 69 | 4-[(Hentricontafluoropentadecyl)methylamino]benzaldehyde |
| 70 | 4-[15-(Trifluoromethyl)-12-pentadecenylamino]benzaldehyde |

TABLE II-continued

The following benzaldehydes are prepared from 4-aminobenzonitrile and the appropriate polyfluoroalkyl halide by the method of Example 58.

| Example No. | Compound |
|---|---|
| 71 | 4-[15-(Trifluoromethyl)-4-pentadecynylamino]-benzaldehyde |
| 72 | 4-[3-(Trifluoromethyl)-2,4,4-trimethylcyclohexylamino]benzaldehyde |

EXAMPLE 73

4-[15-(Trifluoromethyl)pentadecylamino]benzoyl chloride hydrochloride

A cold solution of 25 g. of 4-[15-(trifluoromethyl)pentadecylamino]benzoic acid in 500 ml. dimethoxyethane-methylene chloride (4:1) is prepared and dry hydrochloric acid is bubbled through the solution until no more precipitate forms. The solution is treated with 25 ml. thionyl chloride and refluxed until all of the precipitate has dissolved. The solvents are evaporated to yield 4-[15-(trifluoromethyl)pentadecylamino]benzoyl chloride hydrochloride as an orange, semi-crystalline mass.

EXAMPLE 74

4-[N-Trifluoroacetyl-15-(trifluoromethyl)pentadecylamino]benzoyl chloride

A stirred, ice-cold suspension of 9 g. 4-[15-(trifluoromethyl)pentadecylamino]benzoic acid in 100 ml. of dimethoxyethane and 16 ml. of pyridine is treated with 18 ml. of trifluoroacetic anhydride at 0° C. The solution is stirred at 0° C. for 30 minutes then at temperature and then diluted with 300 ml. ether and 100 g. ice. After stirring vigorously for 15 minutes, the phases are separated, the ether solution is washed with brine, dried and evaporated to a white, amorphous solid.

To a solution of 9.2 g. of the above solid in 30 ml. methylene chloride and 0.5 ml. dimethylformamide is added 5.7 ml. thionyl chloride. After 20 hours at reflux, the solvents are evaporated to yield 4-[N-trifluoroacetyl-15-(trifluoromethyl)pentadecylamino]benzoyl chloride as a light yellow, mobile oil.

EXAMPLE 75

4-[N-Carbobenzyloxy-15-(trifluoromethyl)pentadecylamino]benzoyl chloride

To 15 g. 4-[15-(trifluoromethyl)pentadecylamino]benzoic acid in 200 ml. warm chloroform is added a solution of 15 g. of sodium carbonate in 150 ml. water. To the vigorously stirred solution is added 10 g. carbobenzyloxy chloride. After 2 hours stirring at 40° C., the layers are separated, washed three times with 1 N hydrochloric acid, dried, and evaporated to an oil. The oil is dissolved in 300 ml. toluene, treated with 15 ml. thionyl chloride and the solution is refluxed for 5 hours. The solvents are evaporated and the residue is dissolved three times in toluene, evaporating each time, ultimately to yield 4-[N-carbobenzyloxy-15-(trifluoromethyl)pentadecylamino]benzoyl chloride as a viscous, orange oil.

EXAMPLE 76

1-{4-[N-tert-Butyloxycarbonyl-15-(trifluoromethyl)-pentadecylamino]benzoyl}imidazole A solution of 10 g. of 4-[15-(trifluoromethyl)pentadecylamino]benzoic acid in 100 ml. dioxane is treated with 4.0 g. tert-butylazidoformate and 10 ml. pyridine. After stirring at room temperature for 18 hours, the protected amido-acid is precipitated from solution by the addition of 150 ml. water. The solid is collected, and thoroughly dried, and dissolved in 200 ml. of a mixture consisting of methylene chloride/dimethoxyethane/pyridine (1:4:1). To this solution is added 5.4 g. 1,1'-carbonyldiimidazole. The solution is stirred overnight at room temperature and the solvents are evaporated to yield 1-{4-[N-tert-butyloxycarbonyl-15-(trifluoromethyl)pentadecylamino]benzoyl}imidazole as an orange oil.

EXAMPLE 77

2,3-Dihydroxypropyl 4-[15-(trifluoromethyl)pentadecylamino]benzoate

A solution of 7.34 g. of 4-[15-(trifluoromethyl)pentadecylamino]benzoic acid, 4.80 g. of 25% aqueous sodium hydroxide, and 12.6 g. of 3-iodo-1,2-propanediol in 50 ml. of hexamethylphoshoramide is stirred for 24 hours at ambient temperature, diluted with 100 ml. of ether and stirred for 5 days at ambient temperature. The mixture is treated with water and extracted with ether. The dried extracts are evaporated to yield the product as a white solid.

EXAMPLE 78

Methyl 4-[15-(trifluoromethyl)pentadecylamino]benzoate

A solution of 7.20 g. of 4-[15-(trifluoromethyl)pentadecylamino]benzoic acid in 25 ml. of hexamethylphosphoramide is added to a stirred mixture of 0.800 g. of sodium hydride (57% in mineral oil) and 25 ml. of hexamethylphosphoramide. The solution which forms after one hour is treated with 11.0 g. of methyl iodide and is then stirred at 25° C. for 18 hours. Dilution with water followed by filtration affords a white solid which is crystallized from ethanol to yield the product as a white solid.

EXAMPLE 79

3-Hydroxypropyl 4-[15-(trifluoromethyl)pentadecylamino]benzoate

A mixture of 2.25 g. of methyl 4-[15-(trifluoromethyl)pentadecylamino]benzoate, 280 mg. of 1,3-propanediol and 1.37 g. of p-toluenesulfonic acid is heated at 180° C. for 18 hours and then is partitioned between ether and 3% aqueous sodium carbonate solution. The ether layer is separated, dried, and evaporated to yield the product as a white solid.

EXAMPLE 80

2-Ethoxyethyl 4-[15-(trifluoromethyl)pentadecylamino]benzoate

A solution of 11.8 g. of 4-[15-(trifluoromethyl)pentadecylamino]benzoic acid, 1.00 g. of 2-ethoxyethanol and 5.35 ml. of boron trifluoride etherate in 200 ml. of toluene is stirred under reflux for 48 hours. The solution is treated with an additional 5.35 ml. of boron trifluoride etherate and refluxing is continued for 120 hours. Dilution with water and methylene chloride followed by filtration affords the product as a white solid.

EXAMPLE 81

Isopropyl 4-[15-(trifluoromethyl)pentadecylamino]benzoate

A solution of 50.5 g of 4-[15-(trifluoromethyl)pentadecylamino]benzoic acid and 34.4 ml. of boron trifluoride etherate in 200 ml. of isopropyl alcohol is stirred under reflux for 44 hours, allowed to cool, and poured into 1.20 liters of ice cold 5% aqueous sodium carbonate solution. The white solid is collected by filtration and recrystallized from benzene-ethanol to yield the product as a white solid.

EXAMPLE 82

1-(Methoxycarbonyl)propyl 4-[15-(trifluoromethyl)pentadecylamino]benzoate

To a solution of 10.0 g. 4-[15-(trifluoromethyl)pentadecylamino]benzoyl chloride hydrochloride in 200 ml. methylene chloride is added dropwise a solution of 3 g. methyl α-hydroxybutyrate and 5 g. triethylamine in 100 ml. ether. After 17 hours stirring at room temperature, the precipitate is collected and washed with several portions of ether. The ether solution is washed with water, dried and evaporated to yield the product as a white solid.

EXAMPLE 83

1-(Ethoxycarbonyl)ethyl 4-[15-(trifluoromethyl)pentadecylamino]benzoate

To a warm mixture of 7 g. sodium 4-[15-(trifluoromethyl)pentadecylamino]benzoate in 100 ml. ethanol is added 4.7 g. of ethyl α-tosyloxypropionate. After 17 hours at reflux, the cooled solution is diluted with an equal volume of water and the resultant precipitate is filtered. After washing with cold ethanol and drying, the product is crystallized from acetonitrile to yield the product as colorless crystals.

EXAMPLE 84

1-Carboxyethyl 4-[15-(trifluoromethyl)pentadecylamino]benzoate

A flask containing 10.0 g. 4-[15-(trifluoromethyl)pentadecylamino]benzoic acid, 3.3 g. lactic acid, 500 mg. toluenesulfonic acid and 500 ml. toluene is equipped with a Soxhlet extractor charged with activated 4Å Linde molecular sieves. The solution is refluxed for 24 hours, during which time the Soxhlet extractor is charged twice more with fresh sieves. The hot solution is filtered and allowed to cool, whereupon the product separates as off-white crystals.

EXAMPLE 85

Diethyl O-{4-[15-(trifluoromethyl)pentadecylamino]benzoyl}-tartrate

A mixture of 4-[N-trifluoroacetyl-15-(trifluoromethyl)pentadecylamino]benzoyl chloride and 1.2 g. triethylamine in 100 ml. warm ether is treated with 2.5 g. diethyl tartrate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the product as a white, crystalline solid.

EXAMPLE 86

O-{4-[15-(Trifluoromethyl)pentadecylamino]benzoyl}-malic acid

A warm solution of 4-[N-carbobenzyloxy-15-(trifluoromethyl)pentadecylamino]benzoyl chloride and 1.3 g. triethylamine in 100 ml. ether is treated with 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered, and the solution is evaporated. The residue is crystallized from acetic acid to yield the product as a white solid.

EXAMPLE 87

2-(Ethoxycarbonyl)vinyl 4-[15-(trifluoromethyl)pentadecylamino]benzoate

To a mixture containing 4.3 g. 1-{4-[N-tert-butyloxycarbonyl-15-(trifluoromethyl)pentadecylamino]benzoyl}imidazole, 50 ml. 5 N sodium hydroxide is added 3 g. ethyl α-formyl acetate. The solution is vigorously stirred for 24 hours. The layers are separated, and the chloroform solution is washed once with 50 ml. 1 N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of the product.

TABLE III the following benzoate esters are prepared from the carboxylic acids of Table I (or activated derivatives thereof prepared by the methods of Examples 73–76) by the methods of Examples 77–87 as shown in the table.

| Example No. | Method of Example | Compound |
|---|---|---|
| 88 | 77 | 2,3-Dihydroxypropyl 4-[8-(trifluoromethyl)octylamino]-benzoate |
| 89 | 77 | 2,3-Dihydroxypropyl 4-[16-(pentafluoroethyl)hexadecylamino]benzoate |
| 90 | 77 | 2,3-Dihydroxypropyl 4-[15,15-(difluoro)hexadecylamino]-benzoate |
| 91 | 77 | 2,3-Dihydroxypropyl 4-[6-(pentadecafluoroheptyl)-5-hexenylamino]benzoate |
| 92 | 78 | Methyl 4-[12-(trifluoromethyl)dodecylamino]benzoate |
| 93 | 78 | Methyl 4-[1-hexyl-9-(trifluoromethyl-4-nonynylamino]benzoate |
| 94 | 78 | Methyl 4-[11,11-difluoro-16-(trifluoromethyl)hexadecylamino)benzoate |
| 95 | 78 | Methyl 4-[15,15-(difluoro)-hexadecylamino]benzoate |
| 96 | 79 | 3-Hydroxypropyl 4-[15-(trifluoromethyl)-7-pentadecenylamino]benzoate |
| 97 | 79 | 2-Hydroxypropyl 4-[1-(2,2,2-trifluoroethyl)pentadecylamino[benzoate |
| 98 | 79 | 4-Hydroxybutyl 4-[12-(trifluoromethyl)dodecylamino]-benzoate |
| 99 | 79 | 3-Hydroxypropyl 4-[11,11-(difluoro)dodecylamino]-benzoate |

TABLE III-continued the following benzoate esters are prepared from the carboxylic acids of Table I (or activated derivatives thereof prepared by the methods of Examples 73–76) by the methods of Examples 77–87 as shown in the table.

| Example No. | Method of Example | Compound |
|---|---|---|
| 100 | 80 | 2-Ethoxyethyl 4-[7-(pentadecafluoroheptyl)heptylamino]benzoate |
| 101 | 80 | 3-Methoxypropyl 4-[11-(trifluoromethyl)undecylamino]benzoate |
| 102 | 80 | 2-Ethoxyethyl 4-[3-(2,2,2-trifluoroethyl-2,4,4-trimethylcyclopentylamino]benzoate |
| 103 | 81 | Isopropyl 4-[11-(trifluoromethyl)undecylamino]benzoate |
| 104 | 82 | 1-(Methoxycarbonyl)propyl 4-[6-(trifluoromethyl)hexylamino]benzoate |
| 105 | 82 | 1-(Methoxycarbonyl)ethyl 4-[11-(heptafluoroisopropyl)undecylamino]benzoate |
| 106 | 82 | 1-(Ethoxycarbonyl)propyl 4-(15,15-difluorohexadecylamino)benzoate |
| 107 | 82 | 1-(Methoxycarbonyl)propyl 4-[3-(trifluoromethyl)-2,4,4-trimethylcyclohexylamino]benzoate |
| 108 | 83 | 1-(Ethoxycarbonyl)propyl 4-[11,11-difluoro-16-(trifluoromethyl)hexadecylamino]benzoate |
| 109 | 83 | 1-(Methoxycarbonyl)ethyl 4-[11-(trifluoromethyl)undecylamino]benzoate |
| 110 | 84 | 1-Carboxyethyl 4-[11-(heptafluoropropyl)undecylamino]benzoate |
| 111 | 84 | 1-Carboxyethyl 4-[5-(pentadecafluoroheptyl)-4-pentenylamino]benzoate |
| 112 | 85 | Diethyl O-{4-[(hentricontafluoropentadecyl)methylamino]benzoyl}tartrate |
| 113 | 85 | Diethyl O-{4-[12-fluoro-12-(heptafluoropropyl)-12-(trifluoromethyl)dodecylamino]benzoyl}tartrate |
| 114 | 85 | Diethyl O-{4-(6,6-difluorohexadecylamino)benzoyl]tartrate |
| 115 | 86 | O-{4-[3,7-Dimethyl-7-(trifluoromethyl)octylamino]benzoyl}malic acid |
| 116 | 86 | O-{4-[15-(trifluoromethyl)-7-pentadecenylamino]benzoyl}malic acid |
| 117 | 87 | 2-(Ethoxycarbonyl)vinyl 4-[11-(trifluoromethyl)-9-undecenylamino]benzoate |
| 118 | 87 | 2-(Ethoxycarbonyl)vinyl 4-[11-(trifluoromethyl)undecylamino]benzoate |
| 119 | 87 | 2-(Ethoxycarbonyl)vinyl 4-[5-(pentadecafluoroheptyl)-4-pentenylamino]benzoate |

EXAMPLE 120

1-{4-[15-(Trifluoromethyl)pentadecylamino]benzoyl}-piperidine

To a chilled solution of 35 ml. of piperidine, 2.5 ml. of triethylamine and 0.6 g. of dimethylaminopyridine in 100 ml. of diethyl ether is added (½ hour) a solution of 8.3 g. of 4-[15-trifluoromethyl))pentadecylamino]benzoyl chloride hydrochloride in 50 ml. of ether. The solution is warmed to room temperature and maintained there for two hours. The solution is heated to reflux for an additional 2 hours at which time the reaction is complete. The solution is cooled, extracted twice with water and dried. The solvent is removed in vacuo and the solid is recrystallized from diethyl ether to yield the product as a white solid.

EXAMPLE 121

Ethyl 4-[15-trifluoromethyl)pentadecylamino]hippurate

To a solution of 18.0 g. of 4-[15-(trifluoromethyl)pentadecylamino]benzoic acid in a mixture of dioxane and methylene chloride is added gaseous hydrogen chloride for 10 minutes. The slurry is cooled and 18 ml. of thionyl chloride added. The slurry is brought to reflux for 2 hours and then concentrated under vacuum (thrice diluting with dioxane each time). The amber solution is diluted with 100 ml. of dioxane and this solution added to freshly prepared ethyl glycinate in 300 ml. of methylene chloride containing 1 g. of dimethylaminopyridine and 10 ml. of triethylamine. After 16 hours at room temperature the reaction is refluxed for 2 hours, cooled and filtered. The mother liquor is extracted with water and 10% hydrochloric acid. The solution is dried and concentrated in vacuo to an amber liquid. A sample is pre-absorbed on silica and eluted with ether. Evaporation of the eluate yields a solid which is recrystallized from acetonitrile to yield the product as a white solid.

EXAMPLE 122

N-{4-[15-(Trifluoromethyl)pentadecylamino]benzoyl}glycine

A mixture of 26.4 g. of ethyl 4-[15-(trifluoromethyl)pentadecylamino]hippurate, 110 ml. of 1 N sodium hydroxide solution; and 100 ml. of ethanol is stirred at ambient temperature for 2 hours and then partially evaporated. The aqueous solution is washed with diethyl ether, acidified with 6 N hydrochloric acid, and filtered. The solid is dried in vacuo and recrystallized from acetone to yield the product as a white solid.

EXAMPLE 123

4-[15-(Trifluoromethyl)pentadecylamino]-N-(phenylsulfonyl)benzamide

A solution of 31.4 g. of benzenesulfonamide in 250 ml. of dry dimethylacetamide is added dropwise, with stirring and cooling, to a suspension of 5.5 g. of sodium hydride in 100 ml. of dry dimethylacetamide during 30 minutes at room temperature. Stirring is continued for 30 minutes. In the meantime, a mixture of 36.2 g. of 4-[15-(trifluoromethyl)pentadecylamino]benzoic acid in 100 ml. of methylene chloride, 300 ml. of dimethoxyethane, and 40 ml. of thionyl chloride is refluxed for 1 hour and 15 minutes. The solution is evaporated and to the resulting oil residue is added, in one portion, the previously prepared mixture of sodium benzenesulfonamide in dimethylacetamide. The mixture is stirred for 30 minutes, without cooling, and then filtered. The filtrate is poured into 2 liters of water and 250 ml. of saturated sodium chloride solution. The product is collected by filtration and then dissolved in methylene chloride, the mixture is filtered through diatomaceous earth, and brine is added to break the emulsion. The layers are separated, the organic phase is dried and evaporated.

The residue is crystallized from toluene to yield the product as a white solid.

EXAMPLE 124

N-{4-[15-(Trifluoromethyl)pentadecylamino]benzoyl}-methanesulfonamide

A solution of 25.2 g. of 4-[15-(trifluoromethyl)pentadecylamino]benzoyl chloride hydrochloride and 5.6 g. of methanesulfonamide in 250 ml. of pyridine is stirred under reflux for 2 hours and then concentrated in vacuo. The residue is partitioned between water and diethyl ether; the aqueous layer acidified with 1 N hydrochloric acid, and the organic layer separated, dried over magnesium sulfate and evaporated. Crystallization of the residual white solid from 60% aqueous acetic acid and then from methylene chloride-hexane affords the product as a white solid.

EXAMPLE 125

N-{4-[15-(Trifluoromethyl)pentadecylamino]benzoyl}-alanine

A solution of 4.75 g of 4-[N-trifluoroacetyl-15-(trifluoromethyl)pentadecylamino]benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the product as a white, crystalline solid.

EXAMPLE 126

N-{4-[15-(Trifluoromethyl)pentadecylamino]benzoyl}-benzamide

One gram of a 50% oil dispersion of sodium hydride is washed with petroleum ether by decantation, dried, and suspended in 5 ml. of tetrahydrofuran. To this stirred mixture is added a solution of 2.42 g. of benzamide in 5 ml. of tetrahydrofuran in one portion. An initial hydrogen evolution is observed. While stirring (30 minutes), the sodium hydride gradually disappears and a white, milky, turbid mixture forms. A solution of 0.9 g. of 4-[N-trifluoroacetyl-15-(trifluoromethyl)pentadecylamino]benzoyl chloride in 3 ml. of tetrahydrofuran is added dropwise during 5 minutes to the mixture. The whole milky mixture is stirred at room temperature under nitrogen for one hour. The mixture is then poured into water and extracted with ether. The ether extract is washed with water and brine and dried over sodium sulfate. Evaporation of the solvent, affords a pale yellow solid. The solid is recrystallized from ether/acetonitrile (50/50) and then from acetonitrile to yield the product as a white solid.

EXAMPLE 127

1-{4-[15-(Trifluoromethyl)pentadecylamino]benzoyl}-pyrrolidine

To a warm solution of 4-[N-carbobenzoyloxy-15-(trifluoromethyl)pentadecylamino]benzoyl chloride and 1.3 g. of triethylamine in 100 ml. ether is added 1.2 g. of pyrrolidine. An immediate precipitate forms, the mixture is refluxed for one hour and then filtered. The solid is extracted several times with hot ether, and the ether is evaporated to yield a white solid. The solid is dissolved in tetrahydrofuran (100 ml.) and hydrogenated over 600 mg. 10% palladium-on-carbon at 50 psi. until hydrogen up-take stops. The catalyst is filtered and the filtrate evaporated. The residue is crystallized from acetic acid to yield the product as a white solid.

EXAMPLE 128

N-(2,3-Dihydroxypropyl)-4-[15-(trifluoromethyl)pentadecylamino]benzamide

To a mixture containing 4.3 g. of 1-{4-[N-(tert-butyloxycarbonyl)-4-[15-(trifluoromethyl)pentadecylamino]benzoyl}imidazole, 50 ml. of chloroform, and 50 ml. of 5 N sodium hydroxide is added 1.1 g. of 3-amino-1,2-propanediol. The solution is vigorously stirred for 24 hours, the layers are separated, and the chloroform solution is washed once with 50 ml. of 1 N sodium hydroxide. The solvent is evaporated and the residue is heated for 30 minutes at 40° C. in 50 ml. of anhydrous trifluoroacetic acid. The solvent is again evaporated and the oil is crystallized from acetone to yield the product as a light yellow solid.

TABLE IV

The following benzamides are prepared from the carboxylic acids of Table I (or activated derivatives thereof prepared by the methods of Examples 73–76) by the methods of Examples 120–128 as shown in the table.

| Example No. | Method of Example | Compound |
|---|---|---|
| 129 | 120 | 1-{4-[11-(Trifluoromethyl)-undecylamino]benzoyl}piperidine |
| 130 | 120 | 1-{3-[12-Fluoro-12-(heptafluoropropyl)-12-(trifluoromethyl)dodecylamino]benzoyl}-pyrrolidine |
| 131 | 120 | 1-{4-[5-(Pentadecafluoroheptyl)-4-pentenylamino]benzoyl}-piperidine |
| 132 | 120 | 1-{4-[3-(2,2,2-Trifluoroethyl)-2,4,4-trimethylcyclopentylamino]benzoyl}pyrrolidine |
| 133 | 121 | Ethyl 4-[5-(pentadecafluoroheptyl)pentylamino]hippurate |
| 134 | 121 | Ethyl 4-[7-(trifluoromethylheptylamino]hippurate |
| 135 | 121 | Ethyl 4-[1-hexyl-9-(trifluoromethyl)-4-nonynylamino]hippurate |
| 136 | 121 | Ethyl 4-[3-(trifluoromethyl)-2,4,4-trimethylcyclohexylamino]hippurate |
| 137 | 122 | N-{4-[5-(Pentadecafluoroheptyl)pentylamino]benzoyl}glycine |
| 138 | 122 | N-{4-[7-(Trifluoromethyl)-heptylamino]benzoyl}glycine |
| 139 | 122 | N-{4-[1-Hexyl-9-(trifluoromethyl)-4-nonynylamino]benzoyl}glycine |
| 140 | 122 | N-{4-[3-(Trifluoromethyl)-2,4,4-trimethylcyclohexylamino]benzoyl}glycine |
| 141 | 123 | 4-[14,14-(difluoro)pentadecylamino]-N-(phenylsulfonyl)benzamide |
| 142 | 123 | 4-[15-Trifluoromethyl)-4-pentadecynylamino]-N-(phenylsulfonyl)benzamide |
| 143 | 123 | 4-[18-(Trifluoromethyl)octadecylamino]-N-(phenylsulfonyl)benzamide |
| 144 | 123 | 4-[11-(Nonafluorobutyl)undecylamino]-N-(phenylsulfonyl)-benzamide |
| 145 | 124 | N-{4-[11-(Undecafluoropentyl)-undecylamino]benzoyl}methanesulfonamide |

TABLE IV-continued

The following benzamides are prepared from the carboxylic acids of Table I (or activated derivatives thereof prepared by the methods of Examples 73–76) by the methods of Examples 120–128 as shown in the table.

| Example No. | Method of Example | Compound |
|---|---|---|
| 146 | 124 | N-{4-[11,11-Difluoro-16-(trifluoromethyl)hexadecylamino]benzoyl}methanesulfonamide |
| 147 | 124 | N-[4-(15,15-Difluorohexadecylamino)benzoyl]methanesulfonamide |
| 148 | 125 | N-{4-[15-(Trifluoromethyl)-4-pentadecynylamino]benzoyl}alanine |
| 149 | 125 | N-{4-[7-(Trifluoromethyl)heptylamino]benzoyl}alanine |
| 150 | 126 | N-{4-[1-(2,2,2-Trifluoroethyl)pentadecylamino]benzoyl}benzamide |
| 151 | 126 | N-[4-(11,11-Difluorododecylamino)benzoyl]benzamide |
| 152 | 126 | N-{4-[(Hentricontafluoropentadecyl)methylamino]benzoyl}benzamide |
| 153 | 127 | 1-{4-[16-(pentafluoroethyl)hexadecylamino]benzoyl}pyrrolidine |
| 154 | 127 | 1-{4-[3-(Trifluoromethyl)-2,4,4-trimethylcyclohexylamino]benzoyl}piperidine |
| 155 | 128 | N-(2,3-Dihydroxypropyl)-4-(16,16-difluoroheptadecylamino)benzamide |
| 156 | 128 | N-(2,3-Dihydroxypropyl)-4-[1-(2,2,2-trifluoroethyl)pentadecylamino]benzamide |

EXAMPLE 157

Diethyl 4-[15-(trifluoromethyl)pentadecylamino]benzoylmalonate

A solution of 26.6 g. of diethyl malonate and 10 ml. of 1,2-dimethoxyethane is added to a suspension of 4.0 g. of sodium hydride in 1,2-dimethoxyethane under argon. A solution of 17.3 g. of 4-[15-(trifluoromethyl)pentadecylamino]benzoyl chloride hydrochloride in 1,2-dimethoxyethane is then dded. The reaction mixture is refluxed for 4.5 hours, cooled, poured on ice, acidified, and extracted with ether. The ether solution is washed with water and saturated sodium chloride solution, dried over anhydrous sodium sulfate and concentrated to dryness. Addition of a small amount of ethanol to the residue gives a solid which is filtered and discarded. The ethanol filtrate is concentrated and the residue is recrystallized from ether to yield the product.

EXAMPLE 158 tert-Butyl ethyl 4-[15-(trifluoromethyl)pentadecylamino]benzoylmalonate

A solution of 28.0 g. of tert-butyl ethyl malonate in 10 ml. of 1,2-dimethoxyethane is added to a suspension of 4.0 g. of sodium hydride in 1,2-dimethoxyethane under argon. A solution of 17.3 g. of 4-[15-(trifluoromethyl)pentadecylamino]benzoyl chloride hydrochloride in 1,2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. The residue is then recrystallized from ether to yield the product.

EXAMPLE 159

Ethyl 2-{4-[15-(trifluoromethyl)pentadecylamino]benzoyl}acetoacetate

A solution of 21.6 g. of ethyl acetoacetate and 10 ml. of 1,2-dimethoxyethane is added to a suspension of 4.0 g. of sodium hydride in 1,2-dimethoxyethane under argon. A solution of 17.3 g. of 4-[15-(trifluoromethyl)pentadecylamino]benzoyl chloride hydrochloride in 1,2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. Recrystallization from ether affords the product as a white solid.

EXAMPLE 160

Ethyl 4-[15-(trifluoromethyl)pentadecylamino]benzoylacetate

A solution of 3.0 g. of tert-butyl ethyl 4-[15-(trifluoromethyl)pentadecylamino]benzoylmalonate and 10 ml. of trifluoroacetic acid is warmed with stirring for 3 hours. The solution is poured onto ice and neutralized with potassium hydroxide. The resulting precipitate is collected by filtration, washed with water and dried. Recrystallization from chloroform affords the product as a white solid.

EXAMPLE 161

4-[15-(Trifluoromethyl)pentadecylamino]benzoylacetic acid

Two grams of ethyl 4-[15-(trifluoromethyl)pentadecylamino]benzoylacetate is added to a solution of potassium hydroxide in 50 ml. of 1:9 water-ethanol. The reaction mixture is stirred for 24 hours at room temperature. Careful neutralization with sulfuric acid gives a precipitate which is filtered, washed with water, and dried to yield the product.

EXAMPLE 162

4'-[15-(Trifluoromethyl)pentadecylamino]-2-(methylsulfinyl)acetophenone

To a solution of 5.8 g. of dimethyl sulfoxide, dried over sieves, and 50 ml. of tetrahydrofuran is slowly added 28 ml. of n-butyl lithium (2.42 M in hexane). To this mixture is added 10 g. of methyl 4-[15-(trifluoromethyl)pentadecylamino]benzoate in 200 ml. of tetrahydrofuran. After two hours, the reaction mixture is poured onto ice, acidified with dilute hydrochloric acid and quickly extracted with chloroform. The chloroform extract is washed with water and saturated sodium chloride solution and dried over anhydrous sodium sulfate. Concentration affords a solid which is washed with hexane. The white solid is dried in vacuo to yield the product.

EXAMPLE 163

4'-[15-(Trifluoromethyl)pentadecylamino]-2-(phenylsulfonyl)acetophenone

A solution of 864 mg. of sodium hydride and 5.3 g. of methylphenylsulfone in 20 ml. of 1,2-dimethoxyethane is stirred at 60° C. for one hour under an atmosphere of argon. To this solution is then added a solution of 5.0 g. of methyl 4-[15-(trifluoromethyl)pentadecylamino]benzoate and 50 ml. of tetrahydrofuran and the reaction mixture is stirred at 60° C. for 1.5 hours. The mixture is cooled, poured onto ice, acidified with dilute hydrochloric acid to pH 3 and then extracted with chloroform. The organic layer is separated, washed three times with water and saturated sodium chloride solution, dried over anhydrous sodium sulfate and then concentrated to dryness. The crude solid is chromatographed on silica gel, eluting with methylene chloride to yield the product.

EXAMPLE 164

4'-[15-(Trifluoromethyl)pentadecylamino]-2-(phenylsulfinyl)acetophenone

To a solution of 6.2 g. of methylphenylsulfoxide, dried over sieves, and 50 ml. of tetrahydrofuran is slowly added 28 ml. of n-butyl lithium (2.42 M in hexane). To this mixture is added 10 g. of methyl 4-[15-(trifluoromethyl)pentadecylamino]benzoate in 200 ml. of tetrahydrofuran. After two hours, the reaction mixture is poured into ice, acidified with diluted hydrochloric acid and quickly extracted with chloroform. The chloroform layer is washed with water and saturated sodium chloride solution and dried over anhydrous sodium sulfate. Concentration affords a solid which is washed with 500 ml. of hot hexane, filtered while hot, and then washed with 50 ml. of hexane. The white solid is dried in vacuo yielding the product.

EXAMPLE 165

3-{4-[15-(Trifluoromethyl)pentadecylamino]benzoyl}-2,4-pentanedione

A solution of 28.4 g. of 2,4-pentanedione and 20 ml. of 1,2-dimethoxyethane is added to a suspenison of 13.6 g. of sodium hydride in 220 ml. of 1,2-dimethoxyethane under argon. A solution of 28.7 g. of 4-[15-(trifluoromethyl)pentadecylamino]benzoyl chloride hydrochloride in 1,2-dimethoxyethane is then added. The reaction mixture is stirred at room temperature for 12 hours, cooled, poured on ice-and extracted with ether. The ether solution is washed with water and saturated sodium chloride solution, dried over anhydrous sodium sulfate and concentrated. The residue is then chromatographed over silica gel to yield the product as a white solid.

EXAMPLE 166

3-{4-[15-(Trifluoromethyl)pentadecylamino]benzoyl}-propionic acid

A mixture of 35 g. of 3-(4-acetamidobenzoyl)propionic acid, 700 ml. of methanol and 1.4 ml. of concentrated sulfuric acid is refluxed for 76 hours. The solution is cooled to 35° C. and poured onto 7 g. of anhydrous sodium acetate while stirring. The reaction mixture is stirred in an ice-bath. The solid is collected and washed with cold methanol to yield methyl 3-(4-aminobenzoyl)propionate as a white solid. A mixture of this solid, 9.2 g. of 15-(trifluoromethyl)pentadecyl bromide and 4.2 g. of potassium carbonate is stirred for 20 hours at 125° C. under nitrogen. The mixture is then cooled to 25° C. and 30 ml. of water is added. After stirring, the product is filtered and washed with water. Recrystallization from methanol affords methyl 3-{4-[15-(trifluoromethyl)pentadecylamino]benzoyl}propionate as a white solid.

A solution of 5.4 g. of methyl 3-{4-[15-(trifluoromethyl)pentadecylamino]benzoyl}propionate is stirred with 5.4 g. of potassium hydroxide in 100 ml. of 95% ethanol for 3 hours at reflux. The reaction mixture is cooled, diluted with 50 ml. of ethanol and 100 ml. of water, and neutralized with hydrochloric acid. The solution is cooled to room temperature and filtered. The white solid is washed with 50% aqueous ethanol and dried. The product is recrystallized from ethanol to yield 3-{4-[15-(trifluoromethyl)pentadecylamino]benzoyl}propionic acid as a white crystalline solid.

TABLE V

The following benzamides are prepared from the benzoic acids and benzoate esters of Tables I and II (or activated derivatives thereof prepared by the methods of Examples 73–76) by the methods of Examples 157–166 as shown in the table.

| Example No. | Methods of Example | Compound |
|---|---|---|
| 167 | 157 | Diethyl 4-[(hentricontafluoropentadecyl)methylamino]benzoylmalonate |
| 168 | 157 | Diethyl 4-[15-(trifluoromethyl)-12-pentadecenylamino]benzoylmalonate |
| 169 | 158 | tert-Butyl ethyl 4-(11,11-difluorododecylamino)benzoylmalonate |
| 170 | 158 | tert-Butyl ethyl 4-[12-fluror-12-(heptafluoropropyl)-12-(trifluoromethyl)dodecylamino]benzoylmalonate |
| 171 | 159 | Ethyl 2-{4-[9-(trifluoromethyl)nonylamino]benzoyl}acetoacetate |
| 172 | 159 | Ethyl 2-{4-[11,11-difluoro-16-(trifluoromethyl)hexadecylamino]benzoyl}acetoacetate |
| 173 | 160 | Ethyl 4-(16,16-difluoroheptadecylamino)benzoylacetate |
| 174 | 160 | Ethyl 4-[12-fluoro-12-(heptafluoropropyl)-12-(trifluoromethyl)dodecylamino]benzoylacetate |
| 175 | 161 | 4-(16,16-Difluoroheptadecylamino)benzoylacetic acid |
| 176 | 161 | 4-[12-Fluoro-12-(heptafluoropropyl)-12-(trifluoromethyl)dodecylamino]benzoylacetic acid |
| 177 | 162 | 4'-[11-(Nonafluorobutyl)undecylamino]-2-(methylsulfinyl)acetophenone |
| 178 | 162 | 4'-[12-(Trifluoromethyl)dodecylamino]-2-(methylsulfinyl)acetophenone |
| 179 | 162 | 4'-[3-(Trifluoromethyl)-2,4,4-trimethylcyclohexylamino]-2-(methylsulfinyl)acetophenone |
| 180 | 163 | 4'-(14,14-Difluoropentadecylamino)-2-(phenylsulfonyl)acetophenone |
| 181 | 163 | 4'-[1-(2,2,2-Trifluoroethyl)decylamino]-2-(phenylsulfonyl)acetophenone |
| 182 | 164 | 4'-[7-(Trifluoromethyl)undecylamino]-2-(phenylsulfinyl)acetophenone |
| 183 | 164 | 4'-[1-Hexyl-11-(trifluoromethyl)undecylamino]-2-(phenylsulfinyl)acetophenone |
| 184 | 165 | 3-{4-[13-(Trifluoromethyl)tridecylamino]benzoyl}-2,4-pentanedione |
| 185 | 165 | 3-[4-(15,15-Difluorohexadecylamino)benzoyl]-2,4-pentane- |

TABLE V-continued

The following benzamides are prepared from the benzoic acids and benzoate esters of Tables I and II (or activated derivatives thereof prepared by the methods of Examples 73–76) by the methods of Examples 157–166 as shown in the table.

| Example No. | Methods of Example | Compound |
|---|---|---|
| | | dione |
| 186 | 166 | 3-{4-[3-(2,2,2-Trifluoroethyl)-2,4,4-trimethylcyclopentylamino]benzoyl}propionic acid |
| 187 | 166 | 3-{4-[12-Fluoro-12-(heptafluoropropyl)-12-(trifluoromethyl)dodecylamino]benzoyl}propionic acid |

EXAMPLE 188

4-[15-(Trifluoromethyl)pentadecylamino]phenylacetic acid

A solution of 8.2 g. of 4-aminophenylacetic acid, 150 ml. of absolute ethanol, and 3 ml. of boron trifluoride etherate is heated to reflux for 15 hours. The solution is concentrated by distillation and then evaporated to dryness in vacuo. The residue is dissolved in ethyl ether, washed with aqueous sodium bicarbonate dried and evaporated to yield ethyl 4-aminophenylacetate. A mixture of 5.0 g. of this amine, 9.4 g. of 15-(trifluoromethyl)pentadecyl bromide, 4.2 g. of anhydrous potassium carbonate and 40 ml. of hexamethylphosphoramide is heated at 80° C. for 7 hours. The mixture is then cooled, diluted with water, and extracted with ethyl ether. The ether extracts are washed with water, dried and evaporated. The residue is recrystallized from a mixture of chloroform and hexane, yielding ethyl 4-[15-(trifluoromethyl)pentadecylamino]phenylacetate. A mixture of 6.0 g. of this ester, 7.0 g. of potassium hydroxide and 100 ml. of ethanol-water is heated to reflux for 4 hours. While hot, the mixture is adjusted to pH 7 with concentrated hydrochloric acid. The mixture is diluted with water, cooled and filtered. Recrystallization of the precipitate yields the product as a white solid.

EXAMPLE 189

4-[15-(Trifluoromethyl)pentadecylamino]hydrocinnamic acid

A mixture of 5.0 g. of 4-nitrocinnamic acid and 100 mg. of 10% palladium-on-carbon in 200 ml. of ethanol containing 5 drops of 5.5 N ethanolic hydrogen chloride is treated with hydrogen in a Parr apparatus at room temperature for 3 hours. The mixture is then filtered through celite and the filtrate is concentrated, affording 4-aminohydrocinnamic acid.

A solution of 10.0 g. of 4-aminohydrocinnamic acid in 100 ml. of absolute ethanol containing 16 l ml. of boron trifluoride etherate is heated to reflux for 48 hours. The solution is then cooled, poured into 5% aqueous sodium carbonate, and extracted with methylene chloride. Evaporation of the organic extracts yields ethyl 4-aminohydrocinnamate.

In a manner directly analogous to that described in Example 8, ethyl 4-aminohydrocinnamate is alkylated with 15-(trifluoromethyl)pentadecyl bromide to form ethyl 4-[15-(trifluoromethyl)pentadecylamino]hydrocinnamate. Subsequently, in a manner directly analogous to that described in Example 9, ethyl 4-[15-(trifluoromethyl)pentadecylamino]hydrocinnamate is hydrolyzed to 4-[15-(trifluoromethyl)pentadecylamino]hydrocinnamic acid.

EXAMPLE 190

4-[15-(Trifluoromethyl)pentadecylamino]cinnamic acid

A mixture of ethyl 4-aminocinnamate, one equivalent of 15-(trifluoromethyl)pentadecyl bromide and one equivalent of anhydrous potassium carbonate in hexamethylphosporamide is heated for 20 hours at 60° C. The mixture is then cooled, diluted with water and extracted with ether. The combined ether extracts are dried, filtered and evaporated to provide ethyl 4-[15-(trifluoromethyl)pentadecylamino]cinnamate. The ester is hydrolyzed with sodium hydroxide in a 1:9 water:ethanol solution at steam bath temperatures for 10 hours. The hot solution is then acidified with acetic acid, cooled and filtered and the solid is washed with water. Recrystallization from chloroform yields the product as a white solid.

EXAMPLE 191

4-[15-(Trifluoromethyl)pentadecylamino]phenylpropiolic acid

A sample of 50 g. of ethyl 4-aminocinnamate is dissolved in 500 ml. of ethyl ether and a solution of 28 g. of trifluoroacetic anhydride in 30 ml. of ether is added dropwise. When the addition is complete, the reaction is allowed to stir for another hour. The mixture is then diluted with hexane and filtered, providing ethyl 4-trifluoroacetamidocinnamate.

A solution of 40 g. of ethyl 4-trifluoroacetamido cinnamate in 200 ml. of carbon tetrachloride is cooled in ice. Bromine (28 g.) is added dropwise, the reaction is allowed to stir for one additional hour and then the solvent is evaporated. The crystalline residue is the dibromo ester.

A solution of 11.4 g. of potassium hydroxide in 300 ml. of 95% ethanol is cooled to 40° C. and 20 g. of the crude dibromo ester above is added. After 30 minutes, the reaction is heated to reflux for five hours. The solution is then cooled and filtered. The filtrate is treated with acetic acid until the solution is neutral to litmus, then concentrated, chilled and filtered, to yield 4-aminophenylpropiolic acid.

The 4-aminophenylpropiolic acid is converted to 4-{15-(trifluoromethyl)pentadecylamino]phenylpropiolic acid in the manner of Example 188.

TABLE VI

The following carboxylic acids are prepared by alkylation of the corresponding 4-aminophenyl carboxylate ester with the approriate polyfluoroalkyl halide, trifluoromethanesulfonate, or methanesulfonate followed by hydrolysis using the methods of Examples 188–191 as shown in the table.

| Example No. | Method of Example | Compound |
|---|---|---|
| 192 | 188 | 4-[7-(Trifluoromethyl)heptylamino]phenylacetic acid |
| 193 | 188 | 4-[16-(Trifluoromethyl)hexadecylamino]phenylacetic acid |
| 194 | 188 | 4-[1-Hexyl-11-(trifluoromethyl)octylamino]phenylacetic acid |
| 195 | 188 | 4-(3,3-Difluorotetradecylamino)phenylacetic acid |
| 196 | 189 | 4-[(Hentricontafluoropentadecyl)methylamino]hydrocinnamic acid |
| 197 | 189 | 4-[15-(Trifluoromethyl)-4-pentadecynylamino]hydro- |

TABLE VI-continued

The following carboxylic acids are prepared by alkylation of the corresponding 4-aminophenyl carboxylate ester with the approriate polyfluoroalkyl halide, trifluoromethanesulfonate, or methanesulfonate followed by hydrolysis using the methods of Examples 188-191 as shown in the table.

| Example No. | Method of Example | Compound |
|---|---|---|
| | | cinnamic acid |
| 198 | 189 | 4-[11-(Trifluoromethyl)undecylamino]hydrocinnamic acid |
| 199 | 189 | 4-[1-(2,2,2-Trifluoroethyl)-tridecylamino]hydrocinnamic acid |
| 200 | 190 | 4-[11-(Heptafluoropropyl)-undecylamino]cinnamic acid |
| 201 | 190 | 4-[12-Fluoro-12-(heptafluoropropyl)-12-(trifluoromethyl)-dodecylamino]cinnamic acid |
| 202 | 190 | 4-[15-(Trifluoromethyl)-9-pentadecenylamino]cinnamic acid |
| 203 | 190 | 4-[1-Hexyl-9-(trifluoromethyl)-4-nonylamino]cinnamic acid |
| 204 | 191 | 4-[14-(Trifluoromethyl)tetradecylamino]phenylpropiolic acid |
| 205 | 191 | 4-[3,7-Dimethyl-7-(trifluoromethyl)octylamino]phenylpropiolic acid |
| 206 | 191 | 4-(11,11-Difluorododecylamino)phenylpropiolic acid |
| 207 | 191 | 4-[3-(Trifluoromethyl)-2,4,4-trimethylcyclohexylamino]phenylpropiolic acid |

I claim:
1. A compound of the formula

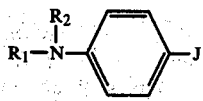

wherein $R_1$ is a saturated or unsaturated hydrocarbon radical of 7-19 carbon atoms which may be branched or unbranched said radical containing one or more perfluorinated (—$CF_2$— or —$CF_3$) carbon atoms excluding the carbon adjacent to the nitrogen atom; $R_2$ is selected from the group consisting of hydrogen or a group convertible in vivo thereinto such as methyl, carboxymethyl, acetyl, succinyl, 1-(sodiumsulfo)loweralkyl, 1-(sodiumsulfo)polyhydroxyalkyl, and 3-phenyl-1,3-bis-(sodiumsulfo)alkyl; and
J is

Z being selected from the group consisting of hydroxy, loweralkoxy, loweralkoxyloweralkoxy, diloweralkylaminoloweralkoxy, hydroxyloweralkoxy, allyloxy, 2,3-epoxypropoxy, benzyloxy, phenoxy, 3-pyridyloxy, pyridylmethoxy, carboxy loweralkoxy, carboxy hydroxyloweralkoxy, tetrahydropyranyloxy, hydroxy alkylamino, allylamino, propargylamino, 2-sulfoethylamino, carboxy loweralkylamino, carboloweralkoxy loweralkylamino, loweralkanoylamino, benzoylamino, loweralkanesulfonylamino, benzenesulfonylamino, loweralkanoylhydrazino, hydroxylamino, $C_4$–$C_5$ polymethyleneimino or a pharmaceutically acceptable non-toxic acid-addition or cationic salt thereof.

2. A compound of the formula

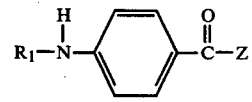

wherein $R_1$ is a saturated or unsaturated hydrocarbon radical of 7-19 carbon atoms which may be branched or unbranched, said radical containing one or more perfluorinated (—$CF_2$— or —$CF_3$) carbon atoms excluding the carbon adjacent to the nitrogen atom; and Z is selected from the group consisting of hydrogen, loweralkyl, hydroxy, loweralkoxy, loweralkoxyloweralkoxy, diloweralkylaminoloweralkoxy, hydroxy loweralkoxy, allyloxy, 2,3-epoxypropoxy, benzyloxy, phenoxy, 3-pyridyloxy, pyridylmethoxy, carboxy loweralkoxy, carboxy hydroxyloweralkoxy, tetrahydropyranyloxy, hydroxyalkylamino, allylamino, propargylamino, 2-sulfoethylamino, carboxy-loweralkylamino, carboloweralkoxy loweralkylamino, loweralkanoylamino, benzoylamino, loweralkanesulfonylamino, benzenesulfonylamino, loweralkanoylhydrazino, hydroxylamino, polymethyleneimino; or a pharmaceutically acceptable non-toxic acid-addition or cationic salt thereof.

3. A compound of the formula

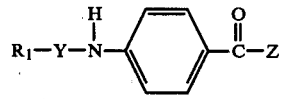

wherein $R_1$ is a saturated loweralkyl group containing one or more perfluorinated (—$CF_2$— or —$CF_3$) carbon atoms excluding the carbon adjacent to the nitrogen atom; Y is a saturated alkylene group containing 6-18 carbon atoms which may be branched or unbranched; and Z is selected from the group consisting of hydroxy, loweralkoxy, loweralkoxyloweralkoxy, diloweralkylaminoloweralkoxy, hydroxyloweralkoxy, allyloxy, 2,3-epoxypropoxy, benzyloxy, phenoxy, 3-pyridyloxy, pyridylmethoxy, carboxy loweralkoxy, carboxy hydroxyloweralkoxy, tetrahydropyranyloxy, hydroxy alkylamino, allylamino, propargylamino, 2-sulfoethylamino, carboxy loweralkylamino, carboloweralkoxy loweralkylamino, loweralkanoylamino, benzoylamino, loweralkanesulfonylamino, benzenesulfonylamino, loweralkanoylhydrazino, hydroxylamino, $C_4$–$C_5$ polymethyleneimino; or a pharmacologically acceptable acid-addition or cationic salt thereof.

4. A compound of the formula

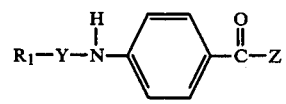

wherein $R_1$ is a saturated loweralkyl group containing one or more perfluorinated (—$CF_2$— or —$CF_3$) carbon atoms excluding the carbon adjacent to the nitrogen atom; Y is a saturated alkylene group containing 11-16 carbon atoms which may be branched or unbranched; and Z is selected from the group consisting of hydroxy, loweralkoxy, loweralkoxyloweralkoxy, diloweralkylaminoloweralkoxy, hydroxyloweralkoxy, allyloxy, 2,3-epoxypropoxy, benzyloxy, phenoxy, 3-pyridyloxy, pyridylmethoxy, carboxy loweralkoxy, carboxy hydroxyloweralkoxy, tetrahydropyranyloxy, hydroxy alkylamino, allylamino, propargylamino, 2-sulfoethylamino, carboxy loweralkylamino, carboloweralkoxy loweralkylamino, loweralkanoylamino, benzoylamino, loweralkanesulfonylamino, benzenesulfonylamino, loweralkanoylhydrazino, hydroxylamino, $C_4$-$C_5$ polymethyleneimino; or a pharmacologically acceptable acid-addition or cationic salt thereof.

5. The compound 4-[11-(trifluoromethyl)undecylamino]benzoic acid.

6. The compound 4-[15-(trifluoromethyl)pentadecylamino]benzoic acid.

7. The compound ethyl 4-[15-(trifluoromethyl)pentadecylamino]benzoate.

8. The compound sodium 4-[15-(trifluoromethyl)pentadecylamino]benzoate.

9. The compound 2,3-dihydroxypropyl 4-[15-(trifluoromethyl)pentadecylamino]benzoate.

10. The compound 4-[(pentadecafluoroheptyl)methylamino]benzoic acid.

11. The compound 4-[16-(pentafluoroethyl)hexadecylamino]benzoic acid.

12. The compound 4-[11-(heptafluoropropyl)undecylamino]benzoic acid.

13. The compound 4-(15,15-difluorohexadecylamino)benzoic acid.

14. The compound 4-[(hentricontafluoropentadecyl)methylamino]benzoic acid.

15. The compound 4-[11-(trifluoromethyl)-9-undecenylamino]benzoic acid.

16. The method of inhibiting atherosclerotic lesion development in mammal comprising the administration of an effective lesion-development inhibiting amount of a compound of claim 1 to said mammal.

17. The method of inhibiting atherosclerotic lesion development in a mammal comprising the administration of an effective lesion-development inhibiting amount of a compound of claim 2 to said mammal.

18. The method of claim 16, wherein said compound is administered to provide a daily dosage of from about one mg. to about 250 mg. per kilogram of body weight of said mammal.

19. The method of claim 17, wherein said compound is administered to provide a daily dosage of from about one mg. to about 250 mg. per kilogram of body weight of said mammal.

20. An antiatherosclerotic composition in dosage-unit form useful for preventing or diminishing atherosclerotic lesion formation in mammals comprising from about one mg. to about 250 mg. per kilogram of body weight per daily dosage unit of a compound of claim 1.

21. An antiatherosclerotic composition in dosage-unit form useful for preventing or diminishing atherosclerotic lesion formation in mammals comprising from about one mg. to about 250 mg. per kilogram of body weight per daily dosage unit of a compound of claim 2.

22. The method of inducing regression of atherosclerotic lesion development in a mammal comprising administering to said mammal an effective lesion-regressive amount of a compound of claim 1.

23. The method of inducing regression of atherosclerotic lesion development in a mammal comprising administering to said mammal an effective lesion-regressive amount of a compound of claim 2.

24. The method of claim 22, wherein said compound is administered to provide a daily dosage of from about one mg. to about 250 mg. per kilogram of body weight of said mammal.

25. The method of claim 23, wherein said compound is administered to provide a daily dosage of from about one mg. to about 250 mg. per kilogram of body weight of said mammal.

26. The method of treating hyperlipidemia and hyperlipoproteinemia and/or altering the lipoprotein pattern in a mammal comprising administering to said mammal an effective lipid-altering amount of a compound of claim 1.

27. The method of treating hyperlipidemia and hyperlipoproteinemia and/or altering the lipoprotein pattern in a mammal comprising administering to said mammal an effective lipid-altering amount of a compound of claim 2.

* * * * *